US005661186A

United States Patent [19]
Takaki et al.

[11] Patent Number: 5,661,186
[45] Date of Patent: Aug. 26, 1997

[54] TETRALINYL- AND INDANYL-ETHYLAMIDES

[75] Inventors: Katherine S. Takaki, Middletown, Conn.; Brett T. Watson, Vaerloese, Denmark; Graham S. Poindexter, Old Saybrook; James R. Epperson, Cromwell, both of Conn.

[73] Assignee: Bristol-Myers Squibb Co., Princeton, N.J.

[21] Appl. No.: 576,658

[22] Filed: Dec. 21, 1995

Related U.S. Application Data

[63] Continuation-in-part of Ser. No. 393,962, Feb. 24, 1995, abandoned.

[51] Int. Cl.$^6$ .......................... A61K 31/16; A61K 31/17; C07C 233/04; C07C 271/06
[52] U.S. Cl. .......................... 514/630; 514/506; 514/448; 514/595; 514/624; 564/219; 564/189; 564/204; 564/56; 560/24; 560/37; 549/72
[58] Field of Search .......................... 564/219, 56, 185; 514/630, 595, 448, 506, 530, 532, 534; 549/72; 560/24, 27, 29, 37

[56] References Cited

U.S. PATENT DOCUMENTS

| | | | |
|---|---|---|---|
| 3,308,157 | 3/1967 | Robertson et al. | 564/219 |
| 4,232,014 | 11/1980 | Mathison et al. | 564/185 |
| 5,071,875 | 12/1991 | Horn et al. | 514/613 |
| 5,194,614 | 3/1993 | Andrieux | 544/400 |
| 5,196,454 | 3/1993 | Grauert et al. | 514/654 |
| 5,276,051 | 1/1994 | Lesieur | 514/415 |
| 5,322,843 | 6/1994 | Yous et al. | 514/233.8 |
| 5,541,228 | 7/1996 | Takaki et al. | 514/630 |

FOREIGN PATENT DOCUMENTS

| | | |
|---|---|---|
| 35445/93 | 9/1992 | Australia . |
| 48729/93 | 4/1994 | Australia . |
| 0384917B1 | 2/1989 | European Pat. Off. . |
| 530087 | 8/1992 | European Pat. Off. . |
| WO94/07487 | 4/1994 | WIPO . |
| WO94/26692 | 11/1994 | WIPO . |
| WO9608466A1 | 3/1996 | WIPO . |

OTHER PUBLICATIONS

S. Yous, et al., *J. Med, Chem.*, 35: 1484–1486 (1992).

S. Misztal, "Synthesis and Pharmacological Properties of N–aroyl–β–(1–indanyl)–ethylamines," *Pol. J. Pharmacol. Pharm.*, 1980, 32, 577–585.

*Chemical Abstracts*, vol. 095, No. 7, Aug. 17, 1981, Abstract No. 061825, S. Misztal et al, "Synthesis and Pharmacological Properties of N–aroyl–β–(1–indanyl)–ethylamines".

Arendt et al, "Alleviation of Jet Lag by Melatonin": preliminary results of controlled double blind trial, *Br. Med. J.* vol. 292, (1986) p. 1170.

Cassone et al, "Dose–Dependent Entrainment of Rat Circadian Rhythms by Daily Injection of Melatonin", *J. Biol. Rhythms*, vol. 1, (1986) pp. 219–229.

Copinga et al, "2–Amido –8–methoxytetralins: A series of Nonindolic Melatonin–like Agents", *J. Med. Chem.*, 36, (1993) pp. 2891–2898.

Ebisawa et al, "Expression cloning of a high–affinity melatonin receptor from Xenopus dermal melanophores", *Proc. Natl. Acad. Sci.*, vol. 91, Jun. (1994) pp. 6133–6177.

Lesieur et al, "Preparation of alkyl(hetero) cyche compound melatonin receptor ligands", CA 125:167 595, (1996).

*Primary Examiner*—José G. Dees
*Assistant Examiner*—Deborah Lambkin
*Attorney, Agent, or Firm*—Sandra M. Nolan; Aldo A. Algieri

[57] ABSTRACT

Certain tetralinyl- and indanyl-ethylamides are useful central nervous system agents.

15 Claims, No Drawings

TETRALINYL- AND INDANYL- ETHYLAMIDES

BACKGROUND

This application is a CIP of Ser. No. 08/393,962 Feb. 24, 1995 abandoned.

This application deals with isomers of certain substituted ethylamides which have drug and bio-affecting properties. Specifically, the invention concerns enantiomers of 6-alkoxyindanyl- and 7-alkoxytetralinyl-substituted ethylamides. All of the compounds discussed herein have melatonergic properties, with some exhibiting greater activity than others.

Melatonin (N-acetyl-5-methoxytryptamine) is a hormone which is synthesized and secreted primarily by the pineal gland. Its chemical structure is:

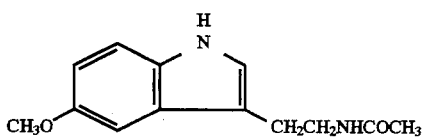

Melatonin levels show a cyclical, circadian pattern with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

Recent evidence demonstrates that melatonin exerts its biological effects through specific receptors. Use of the biologically active, radiolabelled agonist $[^{125}I]$-2-iodomelatonin has led to the identification of high affinity melatonin receptors in the CNS of a variety of species. The sequence of one such high affinity melatonin receptor, cloned from frog dermal melanophores, has been reported (Ebisawa, et al., *Proc. Natl. Acad. Sci.* 91:6133–6137, 1994). In mammalian brain, autoradiographic studies have localized the distribution of melatonin receptors to a few specific structures. Although there are significant differences in melatonin receptor distribution even between closely related species, in general the highest binding site density occurs in discrete nuclei of the hypothalamus. In humans, specific $[^{125}I]$-2-iodomelatonin binding within the hypothalamus is completely localized to the suprachiasmatic nucleus, strongly suggesting the melatonin receptors are located within the human biological clock.

Exogenous melatonin administration has been found to synchronize circadian rhythms in rats (Cassone, et al., *J. Biol. Rhythms*, 1:219–229, 1986). In humans, administration of melatonin has been used to treat jet-lag related sleep disturbances, considered to be caused by desynchronization of circadian rhythms (Arendt, et al., *Br. Med. J.* 292:1170, 1986). Further, the use of a single dose of melatonin to induce sleep in humans has been claimed by Wurtman in International Patent Application WO 94/07487.

The use of melatonin per se may have drawbacks. Binding sites for melatonin have been found in diverse tissues of the body. This means that there is a potential for multiple physiological side effects and low specificity of action. Also, melatonin degrades quickly in vivo and has exhibited low and variable bioavailability.

Thus, melatonin agonists should overcome these drawbacks, while being particularly useful for the treatment of sleep disorders and other chronobiological disorders. Melatonin agonists would also be useful for the further study of melatonin receptor interactions as well as in the treatment of conditions affected by melatonin activity, such as depression, jet-lag, work-shift syndrome, sleep disorders, glaucoma, reproduction, cancer, immune disorders, and neuroendorine disorders.

Aside from simple indole derivatives of melatonin itself, various bicyclic structures have been prepared and their use as melatonin ligands disclosed. In general these bicyclic amide structures can be represented by formula 1:

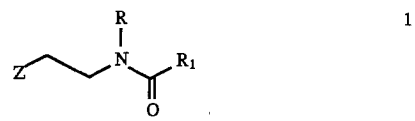

wherein Z is an aryl or heteroaryl system attached by a two carbon bridge to the amide group. Some specific examples follow.

Andrieux et al., in E.P.O. Publication 447 285A, disclose amidoalkylnaphthalenes 2,

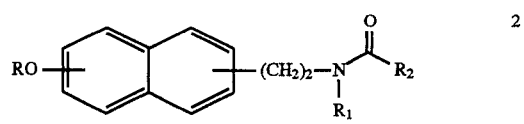

wherein R is lower alkyl; $R_1$ is hydrogen or lower alkyl; and $R_2$ is, inter alia, hydrogen, lower alkyl, or cycloalkyl.

Langlois et al., *J. Med. Chem.*, 38, (1995) pages 2050–60 discusses compounds similar to structure 2, as well as various other substituted ethylamides and ethylamines, as melatonergic agents.

Horn et al., in E.P.O. Publication 420 064A disclose 2-amidotetralins 2 as melatonin ligands,

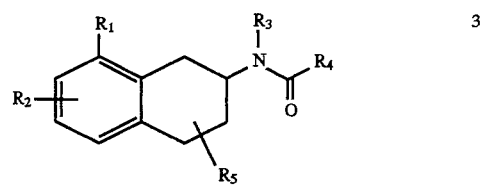

wherein $R_1$ is, inter alia, hydrogen, lower alkyl, or lower alkoxyl; $R_2$ is, inter alia, hydrogen, halogen, or lower alkoxyl; $R_3$ is, inter alia, hydrogen, or lower alkyl; $R_4$ is, inter alia, lower alkyl, haloalkyl or cycloalkyl; and $R_5$ is hydrogen, hydroxyl, halogen, oxo, aryl, lower alkyl or alkylaryl.

Copinga et al, in *J. Med. Chem.*, 1993, 36, p. 2891, discusses amidomethoxytetralins and amido methoxybenzenes of structures 4 and 4a and their melatonergic properties.

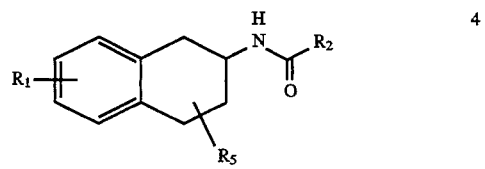

-continued

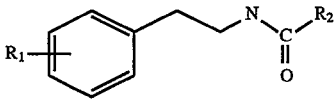

4a

In these structures, $R_1$ is H or $OCH_3$ and $R_2$ is alkyl, haloalkyl, phenylalkyl or phenyl.

Nakamota et al, in EPO Publication No. 0384917A1, published a disclosure of both enantiomers of compound 5, a tetrahydronaphthalenylethylamine acyl derivative:

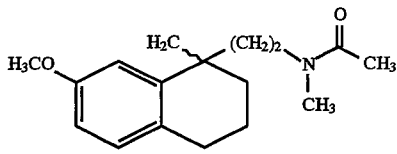

5

The compounds are used as intermediates in the preparation of eptazocine.

The foregoing disclosures do not teach or suggest the melatonergic tetralinyl- or indanyl-ethyl amides of the present invention. The compounds of the present invention display enhanced melatonergic activity, in contradistinction to the prior art, with meta-substitution on the aryl ring in relation to the carbon atom of the saturated ring connecting a C2 bridge to the amide functionality.

SUMMARY AND DETAILED DESCRIPTION OF THE INVENTION

The invention concerns a novel series of melatonergic tetralinyl- and indanyl-ethylamides which conform to formula I or salts, hydrates or isomers thereof:

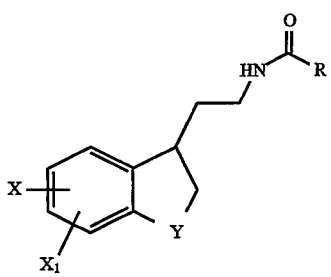

(I)

wherein:

X and $X_1$ are independently hydrogen, halogen, $C_{1-12}$ alkoxy, $C_{1-4}$ fluoroalkoxy, or $C_{1-4}$ alkoxycarbonyl;

Y is $(CH_2)_n$ or $CR_1R_2$ ($R_1$ and $R_2$ selected from H and methyl);

n is 1 or 2; and

R is $C_{1-4}$ alkyl, $C_{1-4}$ alkoxy substituted $C_{1-4}$ alkyl, $C_{3-4}$ cycloalkyl, $C_{2-4}$ alkenyl, $C_{1-3}$ alkylamino, thienyl, or $C_{1-4}$ alkoxy.

One preferred group of compounds are of formula II:

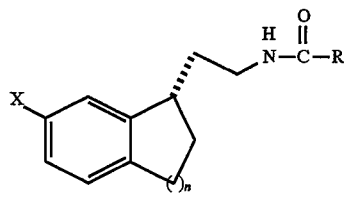

(II)

wherein X, n and R are as defined above. Formula II depicts isomers in which the carbon atom connected to the saturated ring of the indane or tetralin moiety is below the molecular plane.

Another preferred group of compounds are of formula III:

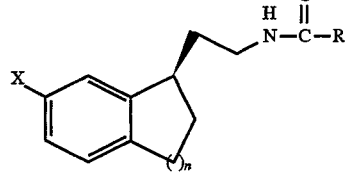

(III)

wherein X, n and R are as defined above. Formula III depicts isomers in which the carbon atom connected to the saturated ring of the indane or tetralin moiety is above the molecular plane.

Compounds of formulas I, II and III, as well as pharmaceutically acceptable hydrates and isomers thereof, are described herein as effective in compositions and methods for melatonergic uses.

"Tetralinyl" refers to 1,2,3,4 tetrahydro-naphthalenyl groups. "Indanyl" relates to 2,3-dihydro-1H-indenyl moieties.

X and $X_1$ are each independently a hydrogen or halogen (i.e., Cl, F, Br or I) moiety, a $C_{1-12}$ alkoxy group, a $C_{1-4}$ fluoroalkoxy group, or a $C_{1-4}$ alkoxycarbonyl group. It is preferred that X be $OCH_3$, F or $OCF_2H$ and that $X_1$ be H or $OCH_3$.

Y is $(CH_2)_n$ or $CR_1R_2$, with $R_1$ and $R_2$ being independently H or methyl.

By "alkoxy" is meant monovalent groups, of the structure: —O-alkyl. "Alkyl" means a monovalent straight or branched chain group of the formula $C_mH_{2m+1}$ or a cyclic group of the formula $C_mH_{2m-1}$, with m being the number of carbon atoms. Cyclopropyl and n-propyl are preferred alkyl groups.

The term "alkoxycarbonyl", refers to alkyl-O—(O)— groups. By "fluoroalkoxy" is meant O-alkyl groups in which the alkyl group bears from 1 to 3, and preferably 2, fluorine atoms.

7-methoxy substituents on the tetralin ring or 6-methoxy substituents on the indane ring are preferred. Also, 7-fluoro substituted tetralins and 6-fluoro substituted indanes are preferred.

β-alkoxy substituents in the amido portion of the molecules (i.e., alkoxy groups on C atoms adjacent to the carbonyl carbon of the amide moiety) are preferred. β-methoxy groups at that site are highly preferred.

The symbol "n" means the integer 1 or 2. Compounds in which n is 1 are slightly more preferred.

R is one $C_{1-4}$ alkyl, $C_{1-4}$ alkoxy substituted $C_{1-4}$ alkyl, $C_{3-4}$ cycloalkyl, $C_{2-4}$ alkenyl, $C_{1-3}$ alkylamino, thienyl, or $C_{1-4}$ alkoxy. In certain preferred compounds, R is selected from $C_{1-4}$ alkyl and $C_{1-4}$ alkoxy substituted $C_{1-4}$ alkyl.

"Cycloalkyl" groups are monovalent cyclic moieties containing at least 3 carbon atoms and conforming to the formula $C_mH_{(2m-1)}$, with m being the number of carbon atoms present.

"Alkenyl" denotes monovalent straight or branched chain moieties containing one site of unsaturation and at least 2 carbon atoms. These moieties conform to the formula $C_mH_{(2m-1)}$, with m being the number of carbon atoms present.

"Alkylamino" refers to —NH-alkyl substituents, preferably —$NHCH_2CH_3$ groups.

"Thienyl" designates the monovalent cyclic $C_4H_3S$ moiety depicted as

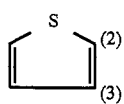

and also known as thiofuran.

The thienyl group is linked to the carbonyl carbon at the 2- or 3-position on the ring. It is preferably linked via the 2 position, so that R is a 2-thienyl moiety.

$R_1$ and $R_2$, are each independently H or methyl moieties. It is preferred that, when present, they both be methyl groups.

"Alkoxy substituted alkyl" groups can be represented by "alkyl-O-alkyl", in which "alkyl" is as defined above and "O" is an oxygen atom. Preferred alkoxy substituted alkyl groups include methoxymethyl and the like.

Preferred compounds have $IC_{50}$ values of 500 nM or less in one or more of the human and rabbit melatonergic binding tests described herein. Thus, applicants have data which tends to show the utility of the subject compounds.

Preferred compounds include those of Formula I in which X is F or methoxy; n is 1 or 2; R is propyl, cyclopropyl or methoxymethyl; and $R_1$ and $R_2$ are both hydrogen or methyl.

Some preferred compounds include:

N-ethyl-N'-[2-(1,2,3,4-tetrahydro-7-methoxy-1-naphthalenyl)ethyl]urea;

N-[2-(1,2,3,4-tetrahydro-7-methoxy-1-naphthalenyl) ethyl]-butanamide;

N-[2-(5-methoxy-1,2,3,4-tetrahydro-1-naphthalenyl) ethyl]-butanamide;

N-[2-(7-methoxy-1,2,3,4-tetrahydro-1-naphthalenyl) ethyl]methyl carbamate;

N-[2-(7-methoxy-1,2,3,4-tetrahydro-1-naphthalenyl) ethyl]-2-methylpropanamide;

N-[2-(7-methoxy-1,2,3,4-tetrahydro-1-naphthalenyl) ethyl]-cyclopropane carboxamide;

N-[2-(7-methoxy-1,2,3,4-tetrahydro-1-naphthalenyl) ethyl]acetamide;

N-[2-(7-methoxy-1,2,3,4-tetrahydro-1-naphthalenyl) ethyl]-propanamide;

N-[2-(7-methoxy-1,2,3,4-tetrahydro-1-naphthalenyl) ethyl]-cyclobutane carboxamide;

N-[2-(7-methoxy-1,2,3,4-tetrahydro-1-naphthalenyl) ethyl]-propanamide;

N-[2-(7-methoxy-1,2,3,4-tetrahydro-1-naphthalenyl) ethyl]-2-methylpropenamide;

N-[2-(7-methoxy-1,2,3,4-tetrahydro-1-naphthalenyl) ethyl]-2-thiophenecarboxamide;

N-[2-(7-methoxy-1,2,3,4-tetrahydro-1-naphthalenyl) ethyl]-2-butenamide;

N-[2-(6-methoxy-1,2,3,4-tetrahydro-1-naphthalenyl) ethyl]-cyclopropane carboxamide;

N-[2-(2,3-dihydro-6-methoxy-1H-inden-1-yl)ethyl] butanamide;

N-[2-(2,3-dihydro-6-methoxy-1H-inden-1-yl)ethyl] cyclopropane carboxamide;

N-[2-(2,3-dihydro-6-methoxy-1H-inden-1-yl)ethyl]-2-methoxyacetamide;

N-[2-(2,3-dihydro-6-methoxy-1H-inden-1-yl)ethyl] acetamide;

N-[2-(6,7-dimethoxy-1,2,3,4-tetrahydro-1-naphthalenyl) ethyl]-cyclopropane carboxamide;

N-[2-(6-methoxy-1,2,3,4-tetrahydro-1-naphthalenyl) ethyl]-butanamide;

N-[2-(6,7-dimethoxy-1,2,3,4-tetrahydro-1-naphthalenyl) ethyl]-2-methoxy acetamide;

N-[2-(1,2,3,4-tetrahydro-1-naphthalenyl)ethyl] cyclopropane carboxamide;

N-[2-(1,2,3,4-tetrahydro-1-naphthalenyl)ethyl]-2-methoxy acetamide;

N-[2-(6,7-dimethoxy-1,2,3,4-tetrahydro-1-naphthalenyl) ethyl]butanamide;

N-[2-(1,2,3,4-tetrahydro-1-naphthalenyl)ethyl] butanamide;

N-[2-(2,3-dihydro-6-methoxy-1H-inden-1-yl)ethyl]-N'-ethyl urea;

N-[2-(5-methoxy-1,2,3,4-tetrahydro-1-naphthalenyl) ethyl]-2-methylpropanamide;

N-[2-(6-methoxy-1,2,3,4-tetrahydro-1-naphthalenyl) ethyl]-2-methoxyacetamide;

N-[2-(2,3-dihydro-6-methoxy-1H-inden-1-yl)ethyl]-2-methylpropanamide;

N-[2-(5-methoxy-1,2,3,4-tetrahydro-1-naphthalenyl) ethyl]acetamide;

(+)-N-[2-(2,3-dihydro-6-methoxy-1H-inden-1-yl)ethyl]-butanamide;

(+)-N-[2-(1,2,3,4-tetrahydro-7-methoxynaphthalen-1-yl) ethyl]methoxyacetamide;

N-[2-(2,3-dihydro-6-methoxy-3,3-dimethyl-1H-inden-1-yl)ethyl]acetamide;

N-[2-(2,3-dihydro-6-methoxy-3,3-dimethyl-1H-inden-1-yl)ethyl]butanamide;

N-[2-(2,3-dihydro-6-dodecyloxy-1H-inden-1-yl)ethyl]butanamide;

N-[2-(2,3-dihydro-6-nonyloxy-1H-inden-1-yl)ethyl]butanamide;

N-[2-(2,3-dihydro-6-methoxy-3,3-dimethyl-1H-inden-1-yl)ethyl]propanamide; and

N-[2-(2,3-dihydro-6-methoxy-3,3-dimethyl-1H-inden-1-yl)ethyl]cyclopropane carboxamide.

Most preferred compounds include:

N-[2-(7-methoxy-1,2,3,4-tetrahydro-1-naphthalenyl) ethyl]-2-methoxyacetamide;

N-[2-(2,3-dihydro-6-methoxy-1H-inden-3-yl)ethyl] butanamide;

N-[2-(2,3-dihydro-6-methoxy-1H-inden-3-yl)ethyl]-2-methylpropanamide;

N-[2-(7-methoxy-1,2,3,4-tetrahydro-1-naphthalenyl) ethyl]acetamide;

N-[2-(7-methoxy-1,2,3,4-tetrahydro-1-naphthalenyl) ethyl]-2-methylpropanamide;

N-[2-(2,3-dihydro-6-methoxy-1H-inden-3-yl)ethyl] cyclopropane carboxamide;

N-[2-(2,3-dihydro-6-methoxy-1-H-inden-3-yl)ethyl] cyclopropane carboxamide;

N-[2-(2,3-dihydro-6-methoxy-1-H-inden-3-yl)ethyl]-2-methoxyacetamide;

N-[2-(7-methoxy-1,2,3,4-tetrahydro-1-naphthalenyl)-ethyl]propanamide;

N-[2-(2,3-dihydro-6-methoxy-1H-inden-3-yl)ethyl] acetamide;

N-[2-(1,2,3,4-tetrahydro-7-methoxy-1-naphthalenyl)-ethyl]butanamide;

N-[2-(7-methoxy-1,2,3,4-tetrahydro-1-naphthalenyl) ethyl]-cyclopropane carboxamide;

N-[2-(7-methoxy-1,2,3,4-tetrahydro-1-naphthalenyl) ethyl]-propenamide;

N-[2-(7-methoxy-1,2,3,4-tetrahydro-1-naphthalenyl)
ethyl]-cyclobutane carboxamide;

N-[2-(7-methoxy-1,2,3,4-tetrahydro-1-naphthalenyl)
ethyl]-2-methylpropenamide;

(−)-N-[2-(2,3-dihydro-6-methoxy-1H-inden-1-yl)ethyl]-
butanamide;

(−)-N-[2-(1,2,3,4-tetrahydro-7-methoxynaphthalen-1-yl)
ethyl]methoxyacetamide;

N-[2-(6-fluoro-2,3-dihydro-1H-inden-1-yl)ethyl]
butanamide;

N-[2-(2,3-dihydro-6-methoxycarbonyl-1H-inden-1-yl)
ethyl]butanamide; and

N-[2-(6-difluoromethoxy-2,3-dihydro-1H-inden-1-yl)
ethyl]butanamide.

Compounds of the invention encompass, in addition to those of the structures shown, all pharmaceutically acceptable solvates, particularly hydrates, thereof.

The present invention also encompasses stereoisomers as well as optical isomers, e.g. mixtures of enantiomers as well as individual enantiomers and diastereomers, which arise as a consequence of structural asymmetry in certain compounds depicted above. Preparation and recovery of the individual isomers is accomplished using procedures discussed herein as well as various methods which are well known to practitioners in the art.

Compounds of Formula I can be prepared using the overall process shown in the following scheme:

General Synthetic Scheme

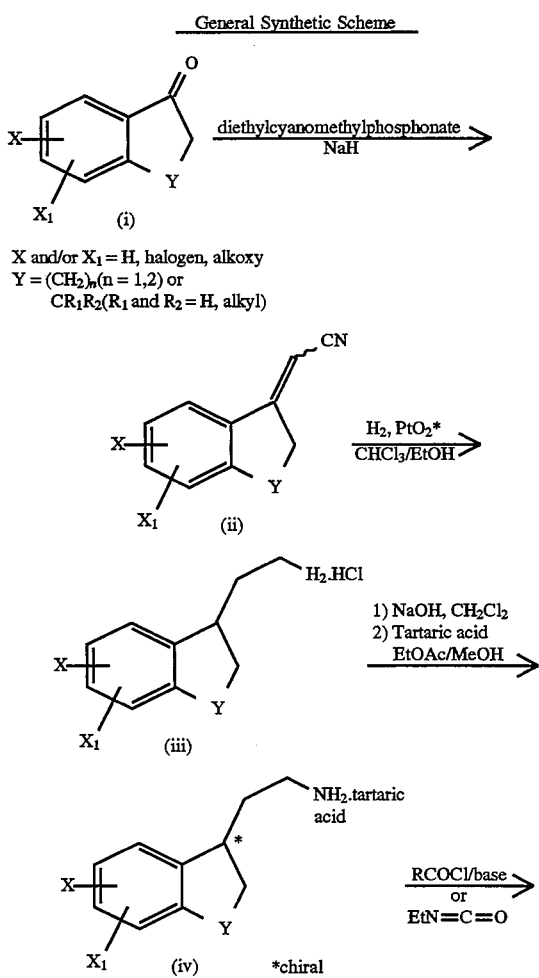

X and/or $X_1$ = H, halogen, alkoxy
Y = $(CH_2)_n$ (n = 1,2) or
$CR_1R_2$ ($R_1$ and $R_2$ = H, alkyl)

-continued
General Synthetic Scheme

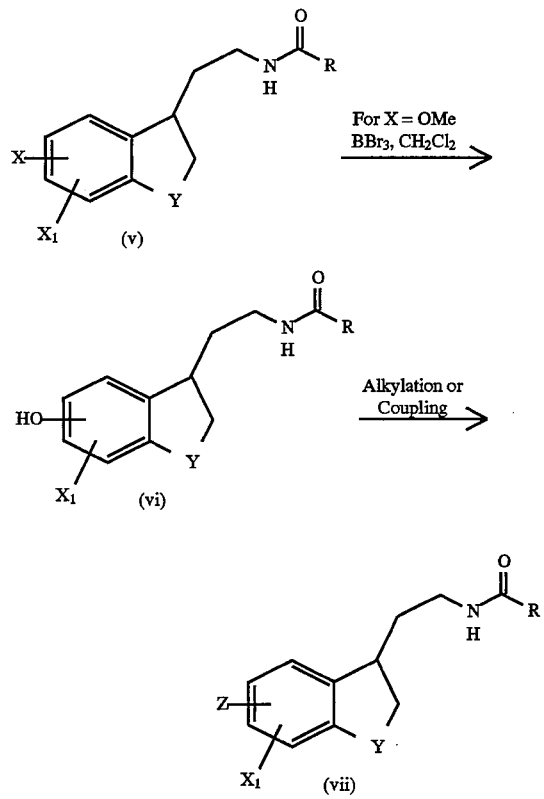

X = alkoxy, arylalkoxy,
alkoxycarbonyl

*Alternatively, the conversion of ii to iii can be carried out using $H_2$, Pd/C, EtOH and $H_2$, Raney nickel, EtOH.

The use of this scheme is described in greater detail below. The ketone starting materials (i) are available from commercial sources or were prepared as described in detail below. The preparation of ii, iii, iv, v, vi and vii are steps 1,2,3,4,5 and 6 respectively. Certain compounds of formula I corresponding to structure v are prepared from iii or iv using General Procedure A or B. Other compounds of formula I corresponding to vii are prepared by demethylation of v (X=OMe) followed by General Procedure C, D or E.

The Compounds

The compounds of the invention are melatonergic agents. They have been found to bind to melatonergic receptor sites in human tissue with good affinity. Accordingly, the compounds and compositions of the invention should be useful as sedatives, chronobiotic agents, anxiolytics, antipsychotics, analgesics, and the like. Specifically, these agents should find use in the treatment of stress, sleep disorders, seasonal depression, appetite regulation, shifts in circadian cycles, melancholia and related conditions. Mammalian hosts, preferably humans, can be treated.

In making pharmaceutical compositions containing compounds of the present invention, the active ingredient(s) will usually be mixed with a carrier, or diluted by a carrier, or enclosed within a carrier which may be in the form of a capsule, sachet or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 0.1 to 500 mg, more usually 1 to 100 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

These active compounds are effective over a wide dosage range. For example, dosages per day will normally fall within the range of about 0.1 to 500 mg. In the treatment of adult humans, the range of about 0.1 to 100 mg/day, in single or divided doses, is preferred. Generally, the compounds of the invention may be used in treating sleep and related disorders in a manner similar to that used for melatonin.

However, it will be understood that the amount of the compound actually administered will be determined by a physician, in the light of relevant circumstances, including the condition to be treated, the choice of compound to be administered, the chosen route of administration, the age, weight, and response of the individual patient, and the severity of the patient's symptoms.

Description of Specific Embodiments

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degrees Celsius and melting points are uncorrected. The nuclear magnetic resonances (NMR) are spectral characteristics refer to chemical shifts (δ) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as a broad singlet (bs), singlet (s), multiplet (m), doublet (d), or triplet (t). Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using the compound neat as a film or by employing potassium bromide (KBr) as diluent. The elemental analyses are reported as percent by weight.

Preparation

The preparation of starting materials and the individual steps of the scheme set out above are described in more detail as follows:

Preparation of Ketone Starting Materials:

Ketone starting materials (i) were purchased commercially or prepared as indicated below.

Synthesis of 6-Methoxy-3,3-dimethylindanone.

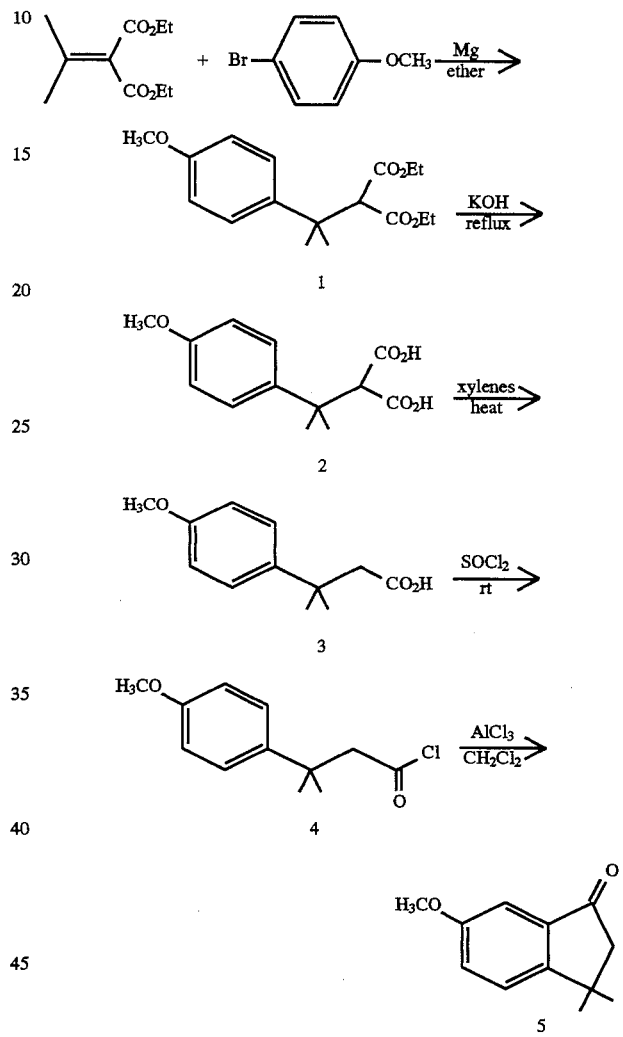

4-Bromoanisole (18.7 g, 0.15 mol) was added to a suspension of Mg (3.6 g, 0.15 mol) in ether (200 ml) and the reaction was initiated with I$_2$ and heat. The remainder of the 4-bromoanisole was added dropwise via addition funnel and the resulting mixture was stirred at room temperature for 1.5 h. CuCl (0.1 g) was added at room temperature and after stirring for 0.5 h the mixture was cooled to 0° C. and diethylisopropylidene malonate (19.5 ml, 0.10 mol) in ether (50 ml) was added dropwise via addition funnel. The mixture was allowed to warm to room temperature and stirred overnight.

Work-up was done by the addition of H$_2$O, followed by careful addition of 6N HCl. The mixture was then diluted with H$_2$O, partioned between H$_2$O and ether, and extracted with ether (3×250 ml). The combined the organic layers were dried over MgSO$_4$ and concentrated under reduced pressure to a brown oil. The crude oil was distilled to a yellow oil which crystallized upon standing. Compound 1, 25.0 g, 81% yield.

A mixture of compound 1 (20.0 g, 0.064 mol) and KOH (7.2, 0.128 mol) in H$_2$O (500 ml) was stirred at reflux overnight. The reaction mixture was cooled, acidified with conc. H$_2$SO$_4$ and extracted with CH$_2$Cl$_2$ (3×300 ml). The combined extracts were dried over MgSO$_4$ and concentrated under reduced pressure to a yellow oil. Compound 2, 14.0 g, 94% yield.

A solution of compound 2 (14.0 g, 0.060 mol) in xylenes (250 ml) was refluxed for 4 h then cooled and concentrated under reduced pressure to a yellow oil. Compound 3, 12.0 g, 96% yield.

A solution of compound 3 (12.0 g, 0.057 mol) in SOCl$_2$ (25 ml) was stirred at room temperature overnight. The reaction mixture was concentrated under reduced pressure to a brown oil. Compound 4, 11.3 g, 87% yield.

A solution of compound 4 (11.3 g, 0.05 mol) in CH$_2$Cl$_2$ (50 ml) was added to a mixture of AlCl$_3$ (8.0 g, 0.06) in CH$_2$Cl$_2$ (200 ml) at room temperature and stirred at room temperature overnight. The reaction mixture was poured onto ice and extracted with CH$_2$Cl$_2$ (3×200 ml). The combined organic layers were dried over MgSO$_4$, concentrated under reduced pressure and chromatographed through silica gel (20% EtOAc/Hex) to a brown oil. Compound 5, 8.1 g, 85% yield.

Synthesis of 6-Fluoroindanone

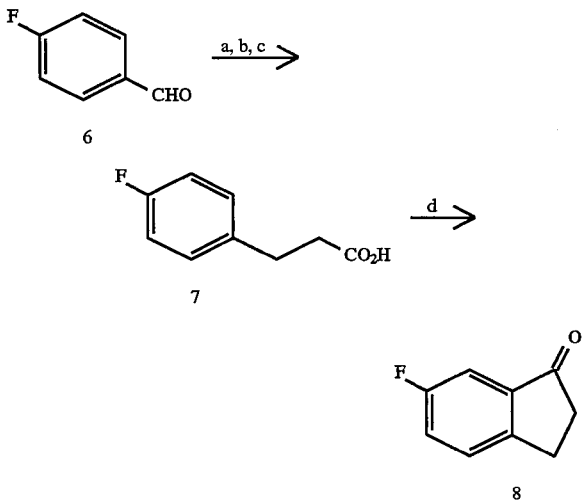

$^a$ malonic acid, pyridine, EtOH.
$^b$ H$_2$, Pd/C, aq NaOH, i-PrOH.
$^c$ aq HCl. $^d$ PPA, 135° C.

A mixture of 4-fluorobenzaldehyde (6, 27.3 g, 0.220 mole), malonic acid (24.9 g, 0.237 mole), and pyridine (9 mL) in 75 mL of EtOH was refluxed 14 h. The reaction then was cooled in an ice bath (0° C.) and filtered. The precipitate was washed with EtOH and air dried to afford 18.3 g (0.110 mole, 50% yield) of the intermediate α,β-unsaturated acid as a colorless white solid: mp 206°–207° C.; $^1$H NMR (DMSO-d$_6$) δ12.39 (br s, 1H), 7.75 (m, 2H), 7.53 (d, 1H, J=16.1 Hz), 7.22 (m, 2H), and 6.48 (d, 1H, J=16.0 Hz); $^{13}$C NMR (DMSO-d$_6$) δ167.5, 163.2 (d, J=247.9 Hz), 142.7, 130.9 (d, J=3.1 Hz), 130.5 (d, J=8.2 Hz), 119.1, and 115.9 (d, J=21.9 Hz). This material was taken up in a mixture of 60 mL of 5% aq NaOH (wt:vol) and 25 mL of i-PrOH and heated to effect dissolution. After the addition of 0.43 g of 10% Pd/C, the mixture was shaken under 60 psi of H$_2$ on a Parr Hydrogenator for 45 min. The mixture was filtered through Celite and the filtrate made acidic with conc HCl. The precipitate was collected by filtration, washed with H$_2$O, and air dried to give 7.41 g (44.1 mmol, 78% yield) of 7 as a colorless solid:

mp 79°–82° C.; $^1$H NMR (DMSO-d$_6$) δ12.13 (br s, 1H), 7.21 (m, 2H), 7.06 (m, 2H), 2.80 (m, 2H), and 2.50 (m, 2H); $^{13}$C NMR (DMSO-d$_6$) δ173.7, 160.7 (d, J=241.2 Hz), 137.0 (d, J=2.5 Hz), 130.0 (d, J=7.9 Hz), 114.9 (d, J=21.1 Hz), 35.3 and 29 5. Anal. Calcd for C$_9$H$_9$FO$_2$: C, 64.28; H, 5.39. Found: C, 64.30; H, 5.45. A mixture of acid 7 (9.41 g, 56.0 mmol) and 125 g of polyphosphoric acid (PPA) was heated in a 135° C. oil bath. After 1.5 h, the mixture was cooled in an ice bath (0° C.) and 400 mL of H$_2$ added. The mixture was stirred for 2 h and the solid collected by filtration. In this manner 6.66 g (44.4 mmol, 79% yield) of 8 was obtained as a waxy yellow solid: $^1$H NMR (DMSO-d$_6$) δ7.60 (m, 1H), 7.48 (m, 1H), 7.31 (m, 1H), 3.04 (m, 2H), and 2.65 (m, 2H); $^{13}$C NMR (DMSO-d$_6$) δ205.4 (d, J=2.9 Hz), 161.6 (d, J=245.2 Hz), 151.1, 128.8 (d, J=8.2 Hz), 122.1 (d, J=23.7 Hz), 108.5 (d, J=21.9 Hz),36.7, and 24.9. HRMS. Calcd for C$_9$H$_8$FO (M+H): 151.0559. Found: 151.0564.

Preparation of the Amine Precursors:
Step 1.
Synthesis of α,β unsaturated nitrile ii.

To a suspension of sodium hydride (0.170 mol) in THF (300ml) was added diethylcyanomethylphosphonate (0.170 mol). The reaction mixture was stirred for 15 min at room temperature (RT). To this was added a solution of the appropriate ketone (0,170 mol) in THF (250 ml) over a 3 h period via an addition funnel. The reaction was stirred at room temperature for 20 h after which a sticky material at the bottom of the reaction vessel was observed. The THF was removed in vacuo and then the residue was extracted into CH$_2$Cl$_2$, washed with H$_2$O, dried (magnesium sulfate) and the solvent was removed to yield a mixture of E and Z isomers.

Step 2.
Preparation of the amine hydrochloride salt iii.

A suspension of the cyano compound from step 1 (0.050 mol), platinum oxide (5%) and CHCl$_3$ (30 ml) in EtOH (100 ml) was charged with H$_2$ at 50 psi and was shaken overnight on a Parr hydrogenation apparatus. The reaction mixture was filtered (filter paper) and the filtrate was concentrated in vacuo to yield a clear oil. Trituration with ether followed by filtration gave a white powder, that corresponds to the hydrochloride salt of the desired amine.

In the case of the tetrahydroindanyl series, the reduction of the α,β-unsaturated cyano compound was carried out under 10 psi pressure and the reaction time was shortened to 4 h.

Step 3.
Resolution of Amines

The HCl salt of the amine was dissolved in water, treated with NaOH (1N) until a basic pH was observed. This was extracted with methylene chloride, dried (MgSO$_4$); the solvent was concentrated in vacuo to yield a solid. This was dissolved in ethyl acetate and treated with D- or L-tartaric acid. Methanol was added to dissolve all solids; this was allowed to stand until a white precipitate was observed, isolated by filtration and repeatedly recrystallized from methanol. The resulting white solid was analyzed by $^1$H NMR. The $^1$H NMR method for determining the enantiomeric excess was performed by the addition of L-trifluorophenylcarbinol to a sample of the amine-salt complex and observing the resonance for the 5-methoxy group of the two enantiomers.

Step 4.
Preparation of Acylated Product:
General Procedure A
Preparation of amide derivatives of Formula I:

Excess triethylamine (0.024 mol) was added to a suspension of the hydrochloride salt of a suitable amine (0.0083 mol) in CH₃CN (150 ml) and the mixture was stirred until starting material was completely dissolved. Alternatively, the free base of the amine, isolated by treatment of the hydrochloride salt with excess 1N sodium hydroxide and extraction into $CH_2Cl_2$, was dissolved in CH₃CN. The appropriate acid chloride (0.0083 mol) was then added, the reaction mixture was stirred overnight, and the acetonitrile was removed in vacuo. The residue was then washed with excess water and extracted into $CH_2Cl_2$. The organic layer was separated, dried (using magnesium sulfate), filtered and concentrated in vacuo to obtain product which was purified by either chromatography or recrystallization.

General Procedure B

Preparation of urea derivatives of Formula I:

The hydrochloride salt of a suitable amine (0.0083 mol) was treated with excess 1N sodium hydroxide. The resulting free base was then dissolved in toluene (100 ml) or $CH_2Cl_2$ and to this was added the appropriate isocyanate (0.0083 mol). The resultant solid was collected by filtration and recrystallized to yield product.

Step 5.

Demethylation to prepare vi.

The appropriate aryl methyl ether (4.05 mmol) was dissolved in methylene chloride (20 mL) and cooled to 0° C. The reaction vessel was enclosed with a rubber septum and flushed with nitrogen. Boron tribromide (8.91 mL of a 1M solution, 8.91 mmol, 2.2 eq) was added to the solution and the solution was allowed to warm to ambient temperature and stirred 16 h (after which TLC analysis indicated complete conversion of ether to phenol). The reaction was quenched with water and extracted with methylene chloride. The organic layers were dried with magnesium sulfate, filtered, and the solvent removed by rotary evaporation to afford the desired phenol.

Step 6.

Preparation of compounds of type vii.

General Procedure C

Preparation of alkoxycarbonyl derivatives vii.

The appropriate phenol (3.52 mmol) was dissolved in pyridine (15 mL) and cooled to 0° C. Trifluoromethanesulfonic anhydride (1.20 g, 4.20 mmol) was added and the reaction was allowed to warm to ambient temperature and stirred 16 h. The reaction was quenched with water and partitioned with ethyl acetate. The combined organic layers were washed with 1N HCl and dried with magnesium sulfate. After filtration and concentration, the crude triflate was used in the following carbomethoxylation procedure.

A solution of the triflate, 1,3-bis(diphenylphosphino) propane (0.041 g, 0.10 mmol), triethylamine (0.40 g), methanol (7 mL), and finally Pd(OAc)₂ (0.23 g, 0.10 mmol) was prepared in DMSO. Carbon monoxide was bubbled into the reaction mixture for 20 min. The reaction vessel was enclosed with a balloon filed with carbon monoxide and heated to 80° C. for 16 h. After cooling to ambient temperature, the reaction mixture was partitioned between ethyl acetate and water. The organic layers were dried with magnesium sulfate, filtered, and concentrated by rotary evaporation. The crude ester was purified by flash chromatography (ethyl acetate/hexane).

General Procedure D

Preparation of alkoxy derivatives of type vii.

A mixture of the appropriate phenol (0.74 mmol), 2 equivalents of a suitable alkyl iodide, and 3 equivalents of powdered potassium carbonate in 12 mL of acetonitrile was heated to reflux for 12 h. The cooled reaction mixture was then filtered through filter paper and concentrated in vacuo. The residue was purified by silica gel column chromatography using ethyl acetate in methylene chloride.

General Procedure E

Preparation of fluoroalkoxy derivatives of type vii.

Chlorodifluoromethane was bubbled into a solution of the appropriate phenol (0.03 mol), NaOH (78 g), dioxane (75 g), and H₂O (75 ml) at 70° C. The reaction was then cooled to room temperature and the dioxane removed under reduced pressure. The residue was partitioned between ether and H₂O and extracted with ether (3×100 ml). The organic layers were combined, dried over MgSO₄, and concentrated under reduced pressure. The crude product was chromatographed through silica gel to provide the final difluoromethyl ether.

These procedures may be varied to produce other compounds which are within the scope of the invention, but not specifically disclosed. One skilled in the art would be aware of appropriate variations. Greater descriptive detail of these processes will be suggested by the specific embodiments below.

The following examples describe in detail the preparation of compounds of Formula I. It will be apparent to those skilled in the art that modifications, both of materials and methods, will allow preparation of other compounds disclosed herein. From the foregoing description and the following examples it is believed that one skilled in the art is able to use the invention to the fullest extent.

Preparation of Compounds

The following examples describe the preparation of compounds of Formula I. They are intended to be illustrative, such that a skilled artisan could make suitable modifications and prepare other compounds of the invention.

Compounds of Formula I which were prepared by general procedure A:

EXAMPLE 1

N-[2-(7-Methoxy-1,2,3,4-tetrahydro-1-naphthalenyl) ethyl]-butanamide. Prepared analogously to Procedure A using n-butyryl chloride. Purified on a silica column using 50% EtOAc/hexane as the solvent system, to obtain a 31% yield of a pale yellow oil that corresponds to product. ¹H NMR (300 MHz, CDCl₃) δ6.95 (d, J=6 Hz, 1H), 6.62–6.66 (m, 2H), 5.67 (bs, 1H), 3.73 (s, 3H), 3.27–3.36 (m, 2H), 2.75–2.81 (m, 1H), 2.63–2.66 (m, 2H), 2.1 (t, J=9 Hz, 2H), 1.76–2.07 (m, 6H), 1.57–1.74 (m, 2H), 0.90 (t, J=6 Hz, 3H); ¹³C NMR (75 MHz, CDCl₃) δ173.0, 157.5, 141.4, 129.9, 129.2, 113.4, 111.7, 55.2, 38.7, 37.6, 36.5, 35.6, 28.7, 27.4, 20.0, 19.2, 13.7; IR (film) 3300, 1650–1500, 1250, 1050 cm⁻¹; MS (DCI) m/e 551 (MH+M), 276 (MH).

EXAMPLE 2

N-[2-(7-Methoxy-1,2,3,4-tetrahydro-1-naphthalenyl) ethyl]methyl carbamate. Prepared analogously to Procedure A using methyl chloroformate. Purified by chromatotron chromatography using 50% EtOAc/hexane as the solvent system. ¹H NMR (300 MHz, CDCl₃) δ6.98 (d, J=8.9 Hz, 1H), 6.68–6.66 (m, 2H), 4.71 (bs, 1H), 3.77 (s, 3H), 3.57 (s, 3H), 3.29 (bs, 2H), 2.82–2.78 (m, 1H), 2.68 (bs,2H), 1.96–1.65 (m, 6H); ¹³C NMR (75 MHz, CDCl₃) δ157.5, 157.0, 141.4, 129.9, 129.1, 113.4, 111.8, 55.3, 52.1, 39.2, 36.9, 35.4, 28.7, 27.4, 19.4; IR (film) 3600–2500, 1710, 1260 cm⁻¹; MS (DCI) m/e 527 (2M+H), 264 (MH); Analysis calc'd for $C_{15}H_{21}NO_3$: C, 68.42; H, 8.04; N, 5.32; found: C, 68.46; H, 8.01; N, 5.19.

EXAMPLE 3

N-[2-(7-Methoxy-1,2,3,4-tetrahydro-1-naphthalenyl) ethyl]-cyclopropane carboxamide. Prepared analogously to Procedure A using cyclopropane carbonyl chloride. Purified by column chromatography using 50% EtOAc/hexane as the solvent system to provide the desired product in 35% yield. $^1$H NMR (300 MHz, CDCl$_3$) δ6.94 (d, J=8.1 Hz, 1H), 6.66–6.63 (m, 2H), 6.35 (bs, 1H), 3.73 (s, 3H), 3.33–3.28 (m, 2H), 2.77–2.76 (m, 1H), 2.64 (bs, 2H), 1.90–1.61 (m, 6H), 1.37–1.34 (m, 1H), 0.92–0.89 (bm, 2H), 0.68–0.65 (bm, 2H); $^{13}$C NMR (75 MHz, CDCl$_3$) δ173.7, 157.5, 141.5, 129.9, 129.2, 113.4, 111.7, 55.2, 37.9, 37.3, 36.5, 30.2, 28.7, 20.0, 14.6, 8.01; IR (film) 3600–2500, 1650, 1250, 1040 cm$^{-1}$; MS (DCI) m/e 547 (MH+M), 274 (MH). Purity 96.7% (HPLC).

EXAMPLE 4

N-[2-(7-Methoxy-1,2,3,4-tetrahydro-1-naphthalenyl) ethyl]-acetamide. Prepared analogously to Procedure A using acetyl chloride. Purified by column chromatography using 50% EtOAc/hexane as the solvent system to provide the desired product in 3% yield. $^1$H NMR (300 MHz, CDCl$_3$) δ6.95 (d, J=8.3 Hz, 1H), 6.66–6.63 (m, 2H), 5.67 (bs, 1H), 3.50 (s, 3H), 3.39–3.24 (m, 2H), 2.81–2.75 (m, 1H), 2.66–2.58 (m, 2H), 1.93 (s, 3H), 1.92–1.61 (m, 6H); $^{13}$C NMR (75 MHz, CDCl$_3$) δ170.12, 157.5, 141.3, 130.2, 129.4, 113.4, 111.7, 55.3, 37.8, 36.4, 35.6, 28.8, 27.5, 23.3, 20.1; IR (film) 3300, 1650, 1560, 1250 cm$^{-1}$; MS (DCI) m/e 495 (MH+M), 248 (MH). 93% purity (HPLC).

EXAMPLE 5

N-[2-(7-Methoxy-1,2,3,4-tetrahydro-1-naphthalenyl) ethyl]-propenamide. Prepared analogously to Procedure A using acryloyl chloride. Purified by column chromatography using 50% EtOAc/hexane as the solvent system to give a 5% yield of a yellow oil that corresponds to product. $^1$H NMR (300 MHz, CDCl$_3$) δ6.94 (d, J=8.2 Hz, 1H), 6.66–6.62 (m, 2H), 6.24 (dd, J=17, 1.78 Hz, 1H), 6.13 (bs, 1H), 6.08 (dd, J=10.02, 17.01 Hz, 1H), 5.58 (dd, J=1.77, 9.9 Hz, 1H), 3.73 (s, 3H), 3.49–3.32 (m, 2H), 2.79–2.66 (m, 1H), 2.64–2.56 (m, 2H), 2.02–1.59 (m, 6H); $^{13}$C NMR (75 MHz, CDCl$_3$) δ165.6, 157.5, 141.3, 131.0, 130.0, 129.2, 126.1, 113.4, 111.7, 55.2, 37.8, 36.4, 35.6, 28.7, 27.5, 20.0; IR (film) 3280, 1655, 1624, 1550, 1250 cm$^{-1}$; MS (DCI) m/e 519 (MH+M), 260 (MH). 97.9% purity (HPLC).

EXAMPLE 6

N-[2-(7-Methoxy-1,2,3,4-tetrahydro-1-naphthalenyl) ethyl]-cyclobutane carboxamide. Prepared analogously to Procedure A using cyclobutane carbonyl chloride. Purified by chromatotron chromatography using 50% EtOAc/hexane as the solvent system to obtain a 32% yield of an oil that corresponds to the product. $^1$H NMR (300 MHz, CDCl$_3$) δ6.93 (d, J=8.1 Hz, 1H), 6.64–6.61 (m, 2H), 5.71 (bs, 1H), 3.74 (s, 3H), 3.34–3.27 (m, 2H), 2.96–2.91 (m, 1H), 2.76–2.75 (m, 1H), 2.65–2.62 (m, 2H), 2.25–2.05 (m, 5H), 1.90–1.30 (m, 7H); $^{13}$C NMR (75 MHz, CDCl$_3$) δ174.9, 157.5, 141.4, 130.0, 129.2, 113.4, 111.7, 55.2, 39.9, 37.5, 36.5, 35.7, 28.7, 27.4, 26.8, 20.0, 18.2; IR (film) 3300, 1640, 1550, 1255, 1040 cm$^{-1}$; MS (DCI) m/e 575 (MH+M), 288 (MH); Analysis calc'd for C$_{18}$H$_{25}$NO$_2$/0.085 H$_2$O: C, 74.70; H, 8.78; N, 4.75; found: C, 74.59; H, 8.70; N, 4.87.

EXAMPLE 7

N-[2-(7-Methoxy-1,2,3,4-tetrahydro-1-naphthalenyl) ethyl]-propanamide. Prepared analogously to Procedure A using propionyl chloride. Purified by chromatotron chromatography using 50% EtOAc/hexane as the solvent system to obtain an 8% yield of an oil that corresponds to the product. $^1$H NMR (300 MHz, CDCl$_3$) δ6.95 (d, J=8.7 Hz, 1H), 6.66–6.63 (m, 2H), 5.49 (bs, 1H), 3.76 (s, 3H), 3.51–3.28 (m, 2H), 2.82–2.76 (m, 1H), 2.67–2.57 (m, 2H), 2.16 (q, J=7.6 Hz, 2H), 2.12 (m, 6H), 1.10 (t, J=4.5 Hz, 3H); $^{13}$C NMR (75 MHz, CDCl$_3$) δ173.7, 157.5, 141.4, 130.0, 129.2, 113.4, 111.7, 55.3, 37.6, 36.5, 35.6, 29.8, 28.7, 27.5, 20.0, 9.9; IR (film) 3300, 1645, 1550, 1250 cm$^{-1}$; MS (DCI) m/e 523 (2M+H), 262 (MH); Analysis calc'd for C$_{16}$H$_{23}$NO$_2$: C, 73.53; H, 8.87; N, 5.36; found: C, 73.32; H, 8.83; N, 5.21.

EXAMPLE 8

N-[2-(2,3-Dihydro-6-methoxy-1H-inden-1-yl)ethyl]-2-methoxyacetamide. Prepared analogously to General Procedure A using methoxy acetyl chloride. Purified by chromatotron chromatography using 50% EtOAc/hexane to provide the desired product in 13% yield. $^1$H NMR (300 MHz, CDCl$_3$) δ7.08 (d, J=8.1 Hz, 1H), 6.73–6.66 (m, 2H), 6.54 (bs, 1H), 3.86 (s, 2H), 3.76 (s, 3H), 3.51–3.38 (m, 2H), 3.37 (s, 3H), 3.14–3.07 (m, 1H), 2.83–2.71 (m, 2H), 2.36–2.25 (m, 1H), 2.11–2.00 (m, 1H), 1.71–1.34 (m, 2H); $^{13}$C NMR (75 MHz, CDCl$_3$) δ169.4, 158.7, 148.0, 135.8, 124.9, 112.3, 109.1, 72.0, 59.2, 55.4, 42.6, 37.2, 34.7, 32.5, 30.6; IR (film) 3320, 1665, 1535, 1280, 1200 cm$^{-1}$; MS (DCI) m/e 527 (MH+M), 264 (MH); Analysis calc'd for C$_{15}$H$_{21}$NO$_3$: C, 68.42; H, 8.04; N, 5.32; found: C, 68.12; H, 8.15; N, 5.11.

EXAMPLE 9

N-[2-(6-Methoxy-1,2,3,4-tetrahydro-1-naphthalenyl) ethyl]-butanamide. Prepared analogously to General Procedure A using n-butyryl chloride. Purified by column chromatography using 50% EtOAc/hexane as the solvent system to provide the desired compound in 38% yield. $^1$H NMR (300 MHz, CDCl$_3$) δ7.03 (d, J=8.5 Hz, 1H), 6.66 (dd, J=8.4, 2.6 Hz, 1H), 6.56 (d, J=2.6 Hz, 1H), 5.64 (bs, 1H),3.73 (s, 3H), 3.38–3.25 (m, 2H), 2.79–2.69 (m, 3H), 2.10 (t, J=7.2 Hz, 2H), 1.90–1.55 (m, 8H), 0.90 (t, J=7.3 Hz, 3H); $^{13}$C NMR (75 MHz, CDCl$_3$) δ172.9, 157.4, 138.3, 132.4, 129.3, 113.6, 111.9, 55.1, 38.7, 37.6, 36.6, 34.6, 29.9, 27.7, 19.7, 19.2, 13.7; IR (film) 3292, 1642, 1552 cm$^{-1}$; MS (DCI) m/e 551 (2M+H), 276 (MH).

EXAMPLE 10

N-[2-(6-Methoxy-1,2,3,4-tetrahydro-1-naphthalenyl) ethyl]-2-methoxyacetamide. Prepared analogously to General Procedure A using methoxy acetyl chloride. Purified by column chromatography using 50% EtOAc/hexane as the solvent system to provide the desired product in 33% yield. $^1$H NMR (300 MHz, CDCl$_3$) δ7.03 (d, J=8.5 Hz, 1H), 6.67 (dd, J=8.4, 2.7 Hz, 1H), 6.57 (d, J=2.6 Hz, 1H), 6.47 (bs, 1H), 3.86 (s, 2H), 3.74 (s, 3H), 3.41–3.33 (m, 2H), 3.38 (s, 3H), 2.80–2.71 (m, 3H), 1.94–1.63 (m, 6H); $^{13}$C NMR (75 MHz, CDCl$_3$) δ169.4, 157.4, 138.3, 132.3, 129.3, 113.6, 111.9, 72.0, 59.1, 55.1, 36.9, 36.6, 34.6, 29.8, 27.7, 19.7; IR (film) 3320, 1664, 1534 cm$^{-1}$; MS (DCI) m/e 278 (MH).

EXAMPLE 11

N-[2-(1,2,3,4-Tetrahydro-1-naphthalenyl)ethyl] butanamide. Prepared according to general procedure A using n-butyryl chloride and purified by elution through silica gel with 20% ethyl acetate/hexanes to provide a yellow oil in 45% yield.: 1H NMR (300 MHz, CDCl$_3$) δ7.01–7.13 (m, 4H), 5.68 (br s, 1H), 3.25–3.42 (m, 2H), 2.79–2.85 (m, 1H), 2.70–2.74 (m, 2H), 2.10 (t, J=7.2 Hz, 2H), 1.56–1.94 (m, 6H), 0.91 (t, J=7.3 Hz, 3H); $^{13}$C NMR (75 MHz, CDCl$_3$) δ173.0, 140.3, 137.1, 129.2, 128.4, 125.7, 125.6, 38.7, 37.6, 36.6, 35.3, 29.5, 27.5, 19.7, 19.2, 13.7; IR (film) 3312, 1648 cm$^{-1}$; MS (FIA, MeOH & NH4OAc) m/e 246 (MH).

EXAMPLE 12

N-[2-(6-Fluoro-2,3-dihydro-1H-inden-1-yl)ethyl] cyclopropane-carboxamide. Prepared according to general procedure A using cyclopropane carbonyl chloride. The compound was isolated in 76%. yield as a pale yellow oil: $^1$H NMR (CDCl$_3$) δ7.10 (m, 1H), 6.81 (m, 2H), 5.77 (br s, 1H), 3.34 (m, 2H), 3.10 (m, 1H), 2.82 (m, 2H), 2.32 (m, 1H), 2.10 (m, m, 1H), 1.73 (m, 1H), 1.30 (m, 1H), 0.94 (m, 2H), and 0.70 (m, 2H); $^{13}$C NMR (CDCl$_3$) δ173.6, 162.0 (d, J=242.9 Hz), 148.8, 139.1, 125.2, (d, J=8.6 Hz), 113.2 (d, J=22.4 Hz), 110.5 (d, J=21.7 Hz), 42.7, 38.1, 34.9, 32.5, 30.7, 14.8, and 7.1. Anal. Calcd for C$_{15}$H$_{18}$FNO: C, 72.85; H, 7.34; N, 5.66. Found: C, 73.08; H, 8.15; N, 5.61. HRMS. Calcd for C$_{15}$H$_{19}$FNO (M+H): 248.1451. Found: 248.1446.

The following compounds of Formula I were also prepared using General Procedure A.

TABLE 1

| Example | Name | mp (°C.) |
|---|---|---|
| 13 | N-[2-(5-Methoxy-1,2,3,4-tetrahydro-1-naphthalenyl)ethyl]butanamide | 71–72 |
| 14 | N-[2-(5-Methoxy-1,2,3,4-tetrahydro-1-naphthalenyl)ethyl]-2-methylpropanamide | 90.5–91.5 |
| 15 | N-[2-(5-Methoxy-1,2,3,4-tetrahydro-1-naphthalenyl)ethyl]acetamide | 84–85 |
| 16 | N-[2-(7-Methoxy-1,2,3,4-tetrahydro-1-naphthalenyl)ethyl]-2-methoxyacetamide | 53–56 |
| 17 | N-[2-(7-Methoxy-1,2,3,4-tetrahydro-1-naphthalenyl)ethyl]-2-methylpropanamide | 54–55 |
| 18 | N-[2-(7-Methoxy-1,2,3,4-tetrahydro-1-naphthalenyl)ethyl]-2-methylpropenamide | 53–56 |
| 19 | N-[2-(7-Methoxy-1,2,3,4-tetrahydro-1-naphthalenyl)ethyl]-2-thiophenecarboxamide | 137–138 |
| 20 | N-[2-(7-Methoxy-1,2,3,4-tetrahydro-1-naphthalenyl)ethyl]-2-butenamide | 79–81 |
| 21 | N-[2-(6-Methoxy-1,2,3,4-tetrahydro-1-naphthalenyl)ethyl]cyclopropane carboxamide | 72–73 |
| 22 | N-[2-(2,3-Dihydro-6-methoxy-1H-inden-1-yl)-ethyl]butanamide | 70–71 |
| 23 | N-[2-(2,3-Dihydro-6-methoxy-1H-inden-1-yl)-ethyl]-2-methylpropanamide | 102–103 |
| 24 | N-[2-(2,3-Dihydro-6-methoxy-1H-inden-1-yl)-ethyl]cyclopropane carboxamide | 103–105 |
| 25 | N-[2-(2,3-Dihydro-6-methoxy-1H-inden-1-yl)-ethyl]acetamide | 71–73 |
| 26 | N-[2-(6,7-Dimethoxy-1,2,3,4-tetrahydro-1-naphthalenyl)ethyl]cyclopropane carboxamide | 80–81 |
| 27 | N-[2-(6,7-Dimethoxy-1,2,3,4-tetrahydro-1-naphthalenyl)ethyl]-2-methoxy acetamide | 73–74 |
| 28 | N-[2-(1,2,3,4-Tetrahydro-1-naphthalenyl)ethyl]-cyclopropane carboxamide | 87–88 |
| 29 | N-[2-(1,2,3,4-Tetrahydro-1-naphthalenyl)ethyl]-2-methoxy acetamide | 45–46 |
| 30 | N-[2-(6,7-Dimethoxy-1,2,3,4-tetrahydro-1-naphthalenyl)ethyl]butanamide | 54–55 |
| 31 | N-[2-(6-Fluoro-2,3-dihydro-1H-inden-1-yl)ethyl]butanamide | 87–89 |
| 32 | N-[2-(2,3-Dihydro-6-methoxy-3,3-dimethyl-1H-inden-1-yl)ethyl]acetamide | 89–90 |
| 33 | N-[2-(2,3-Dihydro-6-methoxy-3,3-dimethyl-1H-inden-1-yl)ethyl]butanamide | 71–72 |
| 34 | N-[2-(2,3-Dihydro-6-methoxy-3,3-dimethyl-1H-inden-1-yl)ethyl]propanamide | 72–74 |
| 35 | N-[2-(2,3-Dihydro-6-methoxy-3,3-dimethyl-1H-inden-1-yl)ethyl]cyclopropane carboxamide | 68–69 |

EXAMPLE 36

(−)-N-[2-(2,3-dihydro-6-methoxy-1H-inden-3-yl)ethyl]-butanamide. N-[2-(2-,3-dihydro-6-methoxy-1H-inden-3-yl) ethyl]amine was resolved with D-tartaric acid using the resolution technique described. The 1:1 amine: D-tartaric acid complex was shown to have an enantiomeric excess of ≦90 by $^1$H NMR. The resolved amine was converted into the butanamide using n-butyryl chloride according to General Procedure A. The resulting white solid was purified by recrytallization from EtOAc/Hexane and shown to be product. m.p. 79°–80° C.; $^1$H NMR (300 MHz, CDCl$_3$) δ7.08 (d, J=8Hz, 1H), 6.72–6.67 (M, 2H), 5.57 (bs, 1H), 3.76 (s, 3H), 3.86–3.66 (bm, 2H), 3.08 (bm, 1H), 2.89–2.69 (bm, 2H), 2.35–2.27 (m, 1H), 2.13 (t, J=7.5 Hz, 2H), 2.06–2.00 (m, 2H), 1.7–1.5 (bm, 4H), 0.92 (t, J=7.2 Hz, 3H); $^{13}$C NMR (75 MHz, CDCl$_3$) δ172.0, 158.8, 148.11, 135.8, 124.9, 112.27, 109.18, 55.48, 42.67, 38.71, 37.98, 34.83, 32.47, 30.55, 19.21, 13.76; IR (KBr) 1632, 1546, 1290 cm$^{-1}$; MS (DCI) 276m/e (MH); Analysis calc'd for C$_{16}$H$_{21}$NO$_1$: C, 78.97; H, 8.70; N, 5.76; found: C, 78.73; H, 8.90; N, 5.76.Analysis calc'd for C$_{16}$H$_{23}$N$_1$O$_2$: C, 73.53; H, 8.87; N, 5.36; found: C, 73.47; H, 8.77; N, 5.13; [α] (25° C., 589 nm, CHCl$_3$)= −5.26

EXAMPLE 37

(+)-N-[2-(2,3-dihydro-6-methoxy-1H-inden-3-yl)]-butanamide. N-[2-(2-,3-dihydro-6-methoxy-1H-inden-3-yl) ethyl]amine was resolved according to the procedure described using L-tartaric acid and was shown to have an enantiomeric excess of ≦90 by $^1$H NMR. The amine was then converted to the butanamide using n-butyryl chloride according to General Procedure A. m.p. 79°–80° C.; $^1$H NMR (300 MHz, CDCl$_3$) δ7.08 (d, J=8Hz, 1H), 6.72–6.67 (M, 2H), 5.57 (bs, 1H), 3.76 (s, 3H), 3.86–3.66 (bm, 2H), 3.08 (bm, 1H), 2.89–2.69 (bm, 2H), 2.35–2.27 (m, 1H), 2.13 (t, J=7.5 Hz, 2H), 2.06–2.00 (m, 2H), 1.7–1.54 (bm, 4H), 0.92 (t, J=7.2 Hz, 3H); $^{13}$C NMR (75 MHz, CDCl$_3$) δ172.0, 158.8, 148.11, 135.8, 124.9, 112.27, 109.18, 55.48, 42.67, 38.71, 37.98, 34.83, 32.47, 30.55, 19.21, 13.76; IR (KBr) 1632, 1546, 1290 cm$^{-1}$; MS (DCI) 276m/e (MH); Analysis calc'd for C$_{16}$H$_{21}$NO$_1$: C, 78.97; H, 8.70; N, 5.76; found: C, 78.73; H, 8.90; N, 5.76. Analysis calc'd for C$_{16}$H$_{23}$N$_1$O$_2$: C, 73.53; H, 8.87; N, 5.36; found: C, 73.47; H, 8.77; N, 5.13; [α] (25° C., 589 nm, CHCl$_3$)=+4.24.

EXAMPLE 38

(−)-N-[2-(1,2,3,4-tetrahydro-7-methoxy naphthalen-1-yl) ethyl]methoxyacetamide. N-[2-(1,2,3,4-tetrahydro-7-methoxy naphthalen-1-yl)ethyl]amine was resolved according to the procedure described using D-tartaric acid and shown to have an enantiomeric excess of 92% by HPLC analysis. The HPLC analyses were performed on a Ultron ES-OVM, 150×4.6 mm column using an isocratic mobile phase at 95/5 (A/B) where A is 20 mM KH$_2$PO$_4$, pH=3.0 and B is acetonitrile. This amine was converted into the amide according to General Procedure A using methoxyacetyl chloride. The final product was purified by recrystallization from EtOAc/hexane to give a white solid. m.p.=61°–63° C.; 1H NMR (300 MHz, CDCl$_3$) δ6.96 (d, J=8 Hz, 1H), 6.67 (s, 1H), 6.65 (m, 1H), 6.51 (bs, 1H), 3.86 (s, 2H), 3.75 (s, 3H), 3.42 (m, 2H), 3.38 (s, 3H), 2.78 (m, 1H), 2.66 (bm, 2H), 1.97–1.76 (bm, 4H), 1.68–1.65 (m, 2H); $^{13}$C NMR (75 MHz, CDCl$_3$) δ169.42, 157.55, 141.23, 130.01, 129.21, 113.34, 111.80, 71.99, 59.15, 55.28, 36.93, 36.45, 35.64, 28.72, 27.51, 20.00; IR (KBr) 1656 cm$^{-1}$; MS (DCI) m/e 278 (MH); Analysis calc'd for C$_{16}$H$_{23}$N$_1$O$_3$: C, 69.29; H, 8.36; N, 5.05; found: C, 69.15; H, 8.33; N, 4.89; [α] (25° C., 589 nm, CHCl$_3$)=−8.33.

EXAMPLE 39

(+)-N-[2-(1,2,3,4-tetrahydro-7-methoxynaphthalen-1-yl) ethyl]methoxyacetamide. N-[2-(1,2,3,4-tetrahydro-7- methoxynaphthalen-1-yl)ethyl]amine was resolved according to the general procedure described in example 1 using L-tartaric add and was shown to have an enantiomeric excess of ≦99% by HPLC analysis. The HPLC analyses were carried out as described in example 3. The amine was converted to the amide according to General Procedure A using methoxyacetyl chloride. The final product was purified by reversed phase HPLC using acetonitrile/water to give a white solid. m.p.=58°–60° C.; $^1$H NMR (300 MHz, CDCl$_3$) δ6.96 (d, J=8 Hz, 1H), 6.67 (s, 1H), 6.65 (m, 1H), 6.50 (bs, 1H), 3.86 (s, 2H), 3.76 (s, 3H), 3.43 (m, 2H), 3.38 (s, 3H), 2.79 (m, 1H), 2.66 (bm, 2H), 1.9–1.7 (bm, 4H), 1.67–1.63 (m, 2H); $^3$C NMR (75 MHz, CDCl$_3$) δ169.44, 157.57, 141.26, 130.03, 129.24, 113.36, 111.82, 72.03, 59.17, 55.30, 36.94, 36.47, 35.66, 28.74, 27.52, 20.02; IR (KBr) 1658 cm$^{-1}$; MS (DCI) m/e (MH)278; Analysis calc'd for $C_{16}H_{23}N_1O_3$: C, 69.29; H, 8.36; N, 5.05; found: C, 69.17; H, 8.37; N, 4.92; [α] (20° C., 589 nm, CHCl$_3$)=+6.96.

Other compounds of Formula I were prepared by general procedure B, as follows:

EXAMPLE 40

N-[2-(7-Methoxy-1,2,3,4-tetrahydro-1-naphthalenyl) ethyl]-N'-ethyl urea. Prepared according to Procedure B. Purified by trituration with ether to provide the desired product in 20% yield. m.p. 70°–71° C; $^1$H NMR (300 MHz, CDCl$_3$) δ6.94 (d, J=6 Hz, 1H), 6.61–6.65 (m, 2H), 4.89 (bs, 2H), 3.72 (s, 3H), 3.24 (bs, 3H), 3.13–3.24 (m, 1H), 2.75–2.79 (m, 1H), 2.63–2.65 (m, 2H), 1.54–1.91 (m, 6H), 1.07 (t, J=6 Hz, 3H); $^{13}$C NMR (75 MHz, CDCl$_3$) δ158.6, 157.5, 141.6, 129.9, 129.2, 113.4, 111.6, 55.2, 38.5, 37.2, 35.5, 35.1, 28.7, 27.4, 19.9, 15.5; IR (KBr) 3300, 1625, 1580, 1250, 1040 cm$^{-1}$; MS (DCI) m/e 553 (MH+M), 277 (MH); Analysis calc'd for $C_{16}H_{24}N_2O_2$: C, 69.53; H, 8.75; N, 10.14; found: C, 69.39; H, 8.61; N, 10.03.

EXAMPLE 41

N-[2-(2,3-Dihydro-6-methoxy-1 H-inden-1-yl)ethyl]-N'-ethyl urea. Prepared according to Procedure B. Purified by multiple recrystallization from EtOAc/Hexanes to provide the desired product in 14% yield. m.p. 90°–92°; $^1$H NMR (300 MHz, CDCl$_3$) δ7.07 (d, J=8.1 Hz, 1H), 6.71 (s, 1H), 6.67 (dd, J=2.4, 9 Hz, 1H), 4.54 (bs, 1H), 4.47 (bs, 1H), 3.75 (s, 3H), 3.27 (q, J=6 Hz, 2H), 3.07–3.19 (m, 3H), 2.70–2.82 (m, 2H), 2.24–2.29 (m, 1H), 1.97–2.03 (m, 1H), 1.54–1.69 (m, 2H), 1.10 (t, J=7 Hz, 3H); $^{13}$C NMR (75 MHz, CDCl$_3$) δ158.6, 158.2, 148.3, 135.8, 124.9, 112.1, 109.1, 55.4, 42.6, 38.9, 35.4, 35.3, 32.5, 30.5, 15.4; IR (KBr) 1626, 1576, 1270 cm$^{-1}$; MS (DCI, isobutane) m/e 263 (MH); Analysis calc'd for $C_{15}H_{22}N_2O_2$: C, 68.67; H, 8.45; N, 10.68; found: C, 68.86; H, 8.53; N, 10.61.

Other compounds of Formula I were prepared by general procedure C, as follows:

EXAMPLE 42

N-[2-(2,3-Dihydro-6-methoxycarbonyl-1H-inden-1-yl) ethyl]butanamide. Prepared according to Procedure C using N-[2-(2,3-Dihydro-6-hydroxy-1H-inden-1-yl)ethyl] butanamide. $^1$H NMR (CDCL$_3$) δ7.85 (d, J=7.0 Hz, 1H), 7.27 (d, J=7.0 Hz, 1H), 7.06 (s, 1H), 5.62 (bs, 1H), 3.90 (s, 3H), 3.39 (t, J=6.2 Hz, 2H), 3.17 (m, 1H), 2.89 (m, 2H), 2.38 (m, 1H), 2.16 (t, J=7.3 Hz, 2H), 2.05 (m, 1H), 1.77 (m, 1H), 1.66 (m, 4H), 1.04 (7, J=6.9 Hz, 3H).

Other compounds of Formula I were prepared by general procedure D, as follows:

EXAMPLE 43

N-[2-(2,3-Dihydro-6-dodecyloxy-1H-inden-1-yl)ethyl] butanamide. Prepared according to procedure D using dodecyliodide. Obtained a 60% yield of the desired product as an off-white solid. m.p. 68°–69°; $^1$H NMR (300 MHz, CDCl$_3$) δ7.07 (d, J=8.1 Hz, 1H), 6.66–6.71 (m, 2H), 5.44 (br s, 1H), 3.89 (t, J=6.6 Hz, 2H), 3.32–3.40 (m, 2H), 3.03–3.10 (m, 1H), 2.68–2.88 (m, 2H), 2.23–2.34 (m, 1H), 2.11 (t, J=7.2 Hz, 2H), 1.97–2.10 (m, 1H), 1.23–1.78 (m, 24H), 0.92 (t, J=7.3 Hz, 3H), 0.85 (t, J=6.9 Hz, 3H), $^{13}$C NMR (75 MHz, CDCl$_3$) δ172.9, 158.2, 148.0, 135.5, 124.8, 109.8, 68.2, 42.6, 38.8, 37.9, 34.8, 32.4, 31.9, 30.5, 29.5, 29.4, 29.3, 26.0, 22.6, 19.1, 14.1, 13.7; IR (KBr) 1636, 1544 cm$^{-1}$; MS m/e 416 (MH+); Analysis calc'd for $C_{27}H_{45}NO_2$: C, 78.02; H, 10.91; N, 3.37; found: C, 78.06; H, 10.92; N, 3.30.

EXAMPLE 44

N-[2-(2,3-Dihydro-6-nonyloxy-1H-inden-1-yl)ethyl] butanamide. Prepared according to procedure D using iodononane. Obtained a 33% yield of the desired product as an off-white solid. m.p. 53°–55°; $^1$H NMR (300 MHz, CDCl$_3$) δ7.07 (d, J=8.1 Hz, 1H), 6.65–6.71 (m, 2H), 5.45 (br, s, 1H), 3.89 (t, J=6.6 Hz, 2H), 3.33–3.40 (m, 2H), 3.05–3.10 (m, 1H), 2.68–2.86 (m, 2H), 2.23–2.34 (m, 1H), 2.11 (t, J=7.3 Hz, 2H), 1.97–2.06 (m, 1H), 1.25–1.78 (m, 18H), 0.92 (t, J=7.3 Hz, 3H), 0.86 (t, J=6.3 Hz, 3H); $^{13}$C NMR (75 MHz, CDCl$_3$) δ172.9, 158.2, 148.0, 135.6, 124.8, 112.8, 109.8, 68.2, 42.6, 38.8, 37.9, 34.8, 32.4, 31.8, 30.5, 29.5, 29.4, 29.3, 29.2, 26.0, 22.6, 19.1, 14.1, 13.7; IR (KBr) 1636, 1544 cm$^{-1}$; MS (electrospray) m/e 372 (M-H$^-$); Analysis calc'd for C24H39NO2: C, 77.16; H, 10.52; N, 3.75; found: C, 77.21; H, 10.76; N, 3.57.

Other compounds of Formula I were prepared by general procedure E, as follows:

EXAMPLE 45

N-[2-(6-Difluoromethoxy-2,3-dihydro-1H-inden-1-yl) ethyl]butanamide. Prepared according to procedure E using N-[2-(2,3-Dihydro-6-hydroxy-1H-inden-1-yl)ethyl] butanamide. Chromatographed through silica gel (50% EtOAc/Hex) to a white solid (100 mg, 11% yield). m.p. 46°–47°; $^1$H NMR (300 MHz, CDCl$_3$) δ7.15 (d, J=8.0 Hz, 1H), 6.87–6.91 (m, 2H), 6.44 (d, J=74 Hz, 1H), 5.43 (br s, 1H), 3.37 (q, J=7.0 Hz, 2H), 3.10 (m, 1H), 2.76–2.88 (m, 2H), 2.28–2.39 (m, 1H), 1.49–2.21 (m, 3H), 1.54–1.79 (m, 5H), 0.92 (t, J=7.3 Hz, 3H); $^{13}$C NMR (75 MHz, CDCl$_3$) δ172.9, 150.0, 148.7, 141.0, 125.3, 119.6, 118.0, 116.2, 115.1, 112.7, 42.6, 38.7, 37.7, 34.8, 32.3, 30.8, 19.1, 13.7; IR (KBr) 3300, 1638, 1552, 1130, 1040 cm$^{-1}$; MS m/e 298 (MH+); Analysis calc'd for $C_{16}H_{21}F_2NO_2$: C, 64.63; H, 7.12; N, 4.71; found: C, 64.64; H, 6.99; N, 4.63.

Melatonergic Binding Activity

The following examples relate to bioassays which demonstrate the melatonergic properties of the compounds of the invention.

EXAMPLE 46

Measurement of Melatonergic Binding at the ML$_1$ Receptor in Rabbit Tissue

1. Reagents
   (a) 50 mM Tris buffer containing 12.5 mM MgCl$_2$, and 2 mM EDTA (pH 7.4 at 37° C).
   (b) Wash buffer: 20 mM Tris base containing 2 mM MgCl$_2$ (pH 7.4 at room temperature).
   (c) 6-Chloromelatonin ($10^{-5}$M final concentration).
   (d) 2-[$^{125}$I]-iodomelatoin, 44 pM final concentration Source: NEN 2. Tissue preparation.

Male New Zealand white rabbits (Hazelton Research) are decapitated, the brains are rapidly removed and chilled. The parietal cortex is crudely dissected and frozen on dry ice with tissue stored at −80° C. until assayed. Tissue is weighed and thawed in 20 mls ice cold Tris buffer (a) and homogenized by treatment with a polytron for 10 seconds at setting 17. Ice cold Tris (a) is added to a volume of 40 mls. The homogenate is centrifuged. The resulting supernatant is decanted and discarded. The pellet is rehomogenized in an additional 20 mls of Tris, diluted and centrifuged. The supernatant is decanted and discarded. The resulting pellet is homogenized in 20 volumes of Tris per gram of original tissue (a 1:20 homogenate), chilled, and held on ice until assayed.

3. Incubation: 37° C. for 1 hour. Reaction is terminated by filtration.

4. Activity: Compounds with an $IC_{50}$ value less than 500 nM are preferred.

5. References: Stankov, B., Cozzi, B., Lucini, V., Fumagalli, P., Scaglione, F. and F. Fraschini. Characterization and mapping of melatonin receptors in the brain of three mammalian species: Rabbit, horse, and sheep. *Neuroendocrinology* 53: 214–221, 1991.

The data generated using the $ML_1$ test on rabbit tissue is believed to be indicative of activity in humans.

The following table sets forth selected compounds and their binding data in $ML_1$ rabbit receptor tests.

TABLE 2

Binding Data of Selected Compounds

| Compound Name | Example | Binding Affinity $IC_{50}$ (nM) |
|---|---|---|
| N-[2-(7-Methoxy-1,2,3,4-tetrahydro-1-naphthalenyl)ethyl]butanamide | 1 | +++ |
| N-[2-(7-Methoxy-1,2,3,4-tetrahydro-1-naphthalenyl)ethyl]cyclopropane carboxamide | 3 | +++ |
| N-[2-(7-Methoxy-1,2,3,4-tetrahydro-1-naphthalenyl)ethyl]acetamide | 4 | +++ |
| N-[2-(7-Methoxy-1,2,3,4-tetrahydro-1-naphthalenyl)ethyl]-2-methoxyacetamide | 16 | +++ |
| N-[2-(2,3-Dihydro-6-methoxy-1H-inden-1-yl)ethyl]-2-methylpropanamide | 17 | +++ |
| N-[2-(2,3-Dihydro-6-methoxy-1H-inden-1-yl)ethyl]butanamide | 22 | +++ |
| N-[2-(2,3-Dihydro-6-methoxy-1H-inden-1-yl)ethyl]cyclopropane carboxamide | 24 | +++ |
| N-[2-(2,3-Dihydro-6-methoxy-1H-inden-1-yl)ethyl]acetamide | 25 | +++ |
| N-[2-(6-Fluoro-2,3-dihydro-1H-inden-1-yl)ethyl]butanamide | 31 | +++ |
| N-[2-(2,3-Dihydro-6-methoxy-3,3-dimethyl-1H-inden-1-yl)ethyl]acetamide | 32 | ++ |
| N-[2-(2,3-Dihydro-6-methoxy-3,3-dimethyl-1H-inden-1-yl)ethyl]butanamide | 33 | ++ |
| (−)-N-[2-(2-,3-dihydro-6-methoxy-1H-inden-3-yl)ethyl]-butanamide. | 36 | +++ |
| (+)-N-[2-(2,3-dihydro-6-methoxy-1H-inden-3-yl)ethyl]-butanamide | 37 | +++ |
| (−)-N-[2-(1,2,3,4-tetrahydro-7-methoxynaphthalen-1-yl)ethyl] methoxyacetamide | 38 | +++ |
| (+)-N-[2-(1,2,3,4-tetrahydro-7-methoxynaphthalen-1-yl)ethyl] methoxyacetamide | 39 | +++ |
| N-[2-(2,3-Dihydro-6-methoxycarbonyl-1H-inden-1-yl)ethyl]butanamide | 42 | +++ |

Binding affinity ranges:
+ = 500 nM or more
++ = 100–500 nM
+++ = 0–100 nM

EXAMPLE 47

Measurement of Melatonergic Binding St the Human Melatonin Receptor $ML_{1A}$

1. Reagents:

(a) 50 mM Tris buffer containing 12.5 mM $MgCl_2$, and 2 mM EDTA, pH 7.4 at 37° C. with concentrated HCl.

(b) Wash buffer: 20 mM Tris base containing 2 mM $MgCl_2$. pH 7.4 at room temperature.

(c) $10^{-4}$M 6-Chloromelatonin ($10^{-5}$M final concentration).

(d) 2-[$^{125}$I]-iodomelatonin, 100 pM final concentration Source: NEN

2. Membrane preparation: The cDNA (human $ML_{1A}$) in pcDNAI was introduced into COS-1 cells by the DEAE-dextran method. Three days after transfection, the media was removed, the plates washed with phosphate buffered saline, the cells removed using Hank's balanced salt solution and pelleted. For preparing membrane homogenates, pellets are thawed on ice, and resuspended in TME buffer, 50 mM Tris base, 12.5 mM $MgCl_2$, 1 mM EDTA (pH7.4 at 37° C. with concentrated HCL), supplemented with 10 μg/ml aprotinin and leupeptin, and 100 μM phenylmethlysulfonylfluoride. The cells were then homogenized using a dounce homogenizer, and centrifuged. The resulting pellet was resuspended with a dounce homogenizer in TME and frozen. On the day of assay, the small aliquot was thawed on ice and resuspended in TME buffer.

3. Incubation: 37° C. for 1 hour. Reaction is terminated by filtration.

4. Activity: Compounds with an $IC_{50}$ value less than 500 nM are preferred.

5. Reference: Reppert, S. M., Weaver, D. R., and Ebisawa, R. (1994), *Neuron*, 13, 1177–1185.

The following table sets forth selected compounds and their binding data at the human melatonin receptor.

| Compound Name | Example | Binding Affinity $IC_{50}$ (nM) |
|---|---|---|
| 1-(−)-N-[2-(2-,3-dihydro-6-methoxy-1H-inden-1-yl)ethyl]-butanamide | 36 | +++ |
| 1-(+)-N-[2-(2,3-dihydro-6-methoxy-1H-inden-1-yl)ethyl]-butanamide | 37 | ++ |
| 1-(−)-N-[2-(1,2,3,4-tetrahydro-7-methoxynaphthalen-1-yl)ethyl] methoxyacetamide | 38 | +++ |
| 1-(+)-N-[2-(1,2,3,4-tetrahydro-7-methoxynaphthalen-1-yl)ethyl] methoxyacetamide | 39 | + |
| N-[2-(2,3-dihydro-6-dodecyloxy-1H-inden-1-yl)ethyl]butanamide | 43 | +++ |
| N-[2-(6-difluoromethoxy-2,3-dihydro-1H-inden-1-yl)ethyl]butanamide | 45 | +++ |

Binding affinity ranges:
+ = 500 nM or more
++ = 100–500 nM
+++ = 0–100 nM

Reasonable variations, such as those which would occur to a skilled artisan, can be made herein without departing from the scope of the invention.

We claim:

1. A compound of formula I or a pharmaceutically acceptable salt, hydrate or isomer thereof:

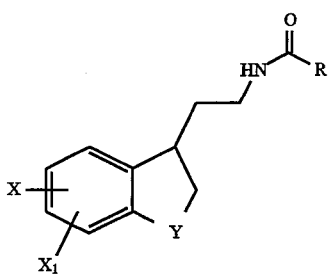

wherein:

X and $X_1$ are independently hydrogen, halogen, $C_{1-12}$ alkoxy, $C_{1-4}$ fluoroalkoxy, or $C_{1-4}$ alkoxycarbonyl;

Y is $(CH_2)_n$ or $CR_1R_2$ ($R_1$ and $R_2$ selected from H and methyl);

n is 1 or 2; and

R is $C_{1-4}$ alkyl, $C_{1-4}$ alkoxy substituted $C_{1-4}$ alkyl, $C_{3-4}$ cycloalkyl, $C_{2-4}$ alkenyl, $C_{1-3}$ alkylamino, thienyl, or $C_{1-4}$ alkoxy.

2. The compound of claim 1 wherein X is a methoxy substituent.

3. The compound of claim 2 wherein R is propyl.

4. The compound of claim 3 selected from the group consisting of:

N-[2-(7-methoxy-1,2,3,4-tetrahydro-1-naphthalenyl)ethyl]butanamide;

N-[2-(7-methoxy-1,2,3,4-tetrahydro-1-naphthalenyl)ethyl]-2-methylpropanamide;

N-[2-(2,3-dihydro-6-methoxy-1H-inden-1-yl)ethyl]butanamide;

N-[2-(2,3-dihydro-6-methoxy-1H-inden-1-yl)ethyl]-2-methylpropanamide;

N-[2-(6-methoxy-1,2,3,4-tetrahydro-1-naphthalenyl)ethyl]butanamide;

N-[2-(6-methoxy-1,2,3,4-tetrahydro-1-naphthalenyl)ethyl]-2-methylpropanamide;

(−)-N-[2-(2-,3-dihydro-6-methoxy-1H-inden-1-yl)ethyl]-butanamide; and (+)-N-[2-(2,3-dihydro-6-methoxy-1H-inden-1-yl)ethyl]-butanamide.

5. The compound of claim 2 wherein R is methoxymethyl.

6. The compound of claim 5 selected from the group consisting of:

N-[2-(2,3-dihydro-6-methoxy-1H-inden-1-yl)ethyl]-2-methoxyacetamide;

N-[2-(6-methoxy-1,2,3,4-tetrahydro-1-naphthalenyl)ethyl]-2-methoxyacetamide;

N-[2-(1,2,3,4-tetrahydro-7-methoxy-1-naphthalenyl)ethyl]-2-methoxy acetamide;

(−)-N-[2-(1,2,3,4-tetrahydro-7-methoxynaphthalen-1-yl)ethyl]methoxyacetamide; and (+)-N-[2-(1,2,3,4-tetrahydro-7-methoxynaphthalen-1-yl)ethyl]methoxyacetamide.

7. The compound of claim 1, (−)-N-[2-(2-,3-dihydro-6-methoxy-1H-inden-1-yl)ethyl]butanamide.

8. The compound of claim 1, (−)-N-[2-(1,2,3,4-tetrahydro-7-methoxynaphthalen-1-yl)ethyl]methoxyacetamide.

9. The compound of claim 1 selected from the group consisting of:

N-[2-(1,2,3,4-tetrahydro-1-naphthalenyl)ethyl]cyclopropane carboxamide;

N-[2-(1,2,3,4-tetrahydro-1-naphthalenyl)ethyl]butanamide;

N-[2-(6-methoxy-1,2,3,4-tetrahydro-1-naphthalenyl)ethyl]cyclopropane carboxamide;

N-[2-(5-methoxy-1,2,3,4-tetrahydro-1-naphthalenyl)ethyl]butanamide;

N-[2-(5-methoxy-1,2,3,4-tetrahydro-1-naphthalenyl)ethyl]-2-methylpropanamide;

N-[2-(5-methoxy-1,2,3,4-tetrahydro-1-naphthalenyl)ethyl]acetamide;

N-[2-(2,3-dihydro-6-methoxy-1H-inden-1-yl)ethyl]butanamide;

N-[2-(2,3-dihydro-6-methoxy-1H-inden-1-yl)ethyl]-2-methylpropanamide;

N-[2-(2,3-dihydro-6-methoxy-1H-inden-1-yl)ethyl]cyclopropane carboxamide;

N-[2-(2,3-dihydro-6-methoxy-1H-inden-1-yl)ethyl]acetamide;

N-[2-(7-methoxy-1,2,3,4-tetrahydro-1-naphthalenyl)ethyl]propenamide;

N-[2-(7-methoxy-1,2,3,4-tetrahydro-1-naphthalenyl)ethyl]acetamide;

N-[2-(7-methoxy-1,2,3,4-tetrahydro-1-naphthalenyl)ethyl]methyl carbamate;

N-[2-(7-methoxy-1,2,3,4-tetrahydro-1-naphthalenyl)ethyl]cyclopropane carboxamide;

N-[2-(7-methoxy-1,2,3,4-tetrahydro-1-naphthalenyl)ethyl]cyclobutane carboxamide;

N-[2-(7-methoxy-1,2,3,4-tetrahydro-1-naphthalenyl)ethyl]propanamide;

N-[2-(6-fluoro-2,3-dihydro-1H-inden-1-yl)ethyl]butanamide;

N-[2-(2,3-dihydro-6-methoxy-3,3-dimethyl-1H-inden-1-yl)ethyl]acetamide;

N-[2-(2,3-dihydro-6-methoxycarbonyl-1H-inden-1-yl)ethyl]butanamide;

N-[2-(2,3-dihydro-6-methoxy-3,3-dimethyl-1H-inden-1-yl)ethyl]butanamide;

N-[2-(6-fluoro-2,3-dihydro-1H-inden-1-yl)ethyl]cyclopropane-carboxamide;

N-[2-(2,3-dihydro-6-methoxy-3,3-dimethyl-1H-inden-1-yl)ethyl]propanamide;

N-[2-(2,3-dihydro-6-methoxy-3,3-dimethyl-1H-inden-1-yl)ethyl]cyclopropane carboxamide;

N-[2-(7-methoxy-1,2,3,4-tetrahydro-1-naphthalenyl)ethyl]-2-methylpropenamide;

N-[2-(7-methoxy-1,2,3,4-tetrahydro-1-naphthalenyl)ethyl]but-2-enamide;

N-[2-(2,3-dihydro-6-dodecyloxy-1H-inden-1-yl)ethyl]butanamide;

N-[2-(6-difluoromethoxy-2,3-dihydro-1H-inden-1-yl)ethyl]butanamide; and

N-[2-(2,3-dihydro-6-nonyloxy-1H-inden-1-yl)ethyl]butanamide.

10. The compound of claim 1 wherein X and Y are methoxy groups.

11. The compound of claim 10 selected from the group consisting of:

N-[2-(6,7-dimethoxy-1,2,3,4-tetrahydro-1-naphthalenyl)ethyl]cyclopropane carboxamide;

N-[2-(6,7-dimethoxy-1,2,3,4-tetrahydro-1-naphthalenyl)ethyl]-2-methoxyacetamide;

N-[2-(6,7-dimethoxy-1,2,3,4-tetrahydro-1-naphthalenyl)
ethyl]butanamide.

12. A method of eliciting a melatonergic effect in a mammal in need thereof comprising the step of administering to said mammal a melatonergic effective amount of a compound of claim 1.

13. The method of claim 12 in the compound is selected from the group consisting of:

(−)-N-[2-(2-,3-dihydro-6-methoxy-1H-inden-1-yl)ethyl]-butanamide;

N-[2-(2,3-dihydro-6-methoxy-1H-inden-1-yl)ethyl]-butanamide;

(−)-N-[2-(1,2,3,4-tetrahydro-7-methoxynaphthalen-1-yl)ethyl]methoxyacetamide;

N-[2-(1,2,3,4-tetrahydro-7-methoxynaphthalen-1-yl)ethyl]methoxyacetamide;

N-[2-(6-fluoro-2,3-dihydro-1H-inden-1-yl)ethyl]butanamide;

N-[2-(2,3-dihydro-6-methoxycarbonyl-1H-inden-1-yl)ethyl]butanamide; and

N-[2-(6-difluoromethoxy-2,3-dihydro-1H-inden-1-yl)ethyl]butanamide.

14. A melatonergic pharmaceutical composition containing a melatonergic effective amount of a compound of claim 1 and a suitable amount of a pharmaceutically acceptable carrier.

15. The composition of claim 11 wherein the compound is selected from the group consisting of:

(−)-N-[2-(2-,3-dihydro-6-methoxy-1H-inden-1-yl)ethyl]-butanamide;

N-[2-(2,3-dihydro-6-methoxy-1H-inden-1-yl)ethyl]-butanamide;

(−)-N-[2-(1,2,3,4-tetrahydro-7-methoxynaphthalen-1-yl)ethyl]methoxyacetamide;

N-[2-(1,2,3,4-tetrahydro-7-methoxynaphthalen-1-yl)ethyl]methoxyacetamide;

N-[2-(6-fluoro-2,3-dihydro-1H-inden-1-yl)ethyl]butanamide;

N-[2-(2,3-dihydro-6-methoxycarbonyl-1H-inden-1-yl)ethyl]butanamide; and

N-[2-(6-difluoromethoxy-2,3-dihydro-1H-inden-1-y)ethyl]butanamide.

* * * * *